US011304990B2

(12) United States Patent
Winqvist et al.

(10) Patent No.: US 11,304,990 B2
(45) Date of Patent: *Apr. 19, 2022

(54) USE OF KNOWN COMPOUNDS—INTRACELLULAR INFECTIONS

(71) Applicant: ISR IMMUNE SYSTEM REGULATION HOLDING AB (PUBL), Stockholm (SE)

(72) Inventors: Ola Winqvist, Uppsala (SE); Emma Lindh, Knivsta (SE); Robert Wallin, Bålsta (SE); Matt Gregory, Cambridge (GB); Steven Moss, Cambridge (GB)

(73) Assignee: ISR IMMUNE SYSTEM REGULATION HOLDING AB (PUBL), Stockholm (SE)

( * ) Notice: Subject to any disclaimer, the term of this patent is extended or adjusted under 35 U.S.C. 154(b) by 128 days.

This patent is subject to a terminal disclaimer.

(21) Appl. No.: 16/479,489

(22) PCT Filed: Jan. 19, 2018

(86) PCT No.: PCT/EP2018/051347
§ 371 (c)(1),
(2) Date: Jul. 19, 2019

(87) PCT Pub. No.: WO2018/134372
PCT Pub. Date: Jul. 26, 2018

(65) Prior Publication Data
US 2019/0374598 A1 Dec. 12, 2019

(30) Foreign Application Priority Data

Jan. 20, 2017 (EP) .................................. 17152449

(51) Int. Cl.
*A61K 38/09* (2006.01)
*A61K 31/568* (2006.01)
*A61K 31/57* (2006.01)

(52) U.S. Cl.
CPC ............ *A61K 38/09* (2013.01); *A61K 31/568* (2013.01); *A61K 31/57* (2013.01)

(58) Field of Classification Search
None
See application file for complete search history.

(56) References Cited

U.S. PATENT DOCUMENTS

| 7,834,141 B1 | 11/2010 | Siler-Khodr |
| 2004/0152639 A1 | 8/2004 | Siler-Khodr |
| 2004/0235748 A1 | 11/2004 | Igari |
| 2004/0259803 A1* | 12/2004 | Boyd ................ A61K 38/08 424/85.2 |
| 2005/0043245 A1 | 2/2005 | Siler-Khodr |
| 2012/0045393 A1 | 2/2012 | Linder |

FOREIGN PATENT DOCUMENTS

| EP | 1382350 A1 | 1/2004 |
| GB | 2237571 A | 5/1991 |
| WO | 200174377 A1 | 10/2001 |
| WO | 200230435 A1 | 4/2002 |
| WO | 2003051272 A2 | 6/2003 |
| WO | 2007144554 A2 | 12/2007 |
| WO | 2009033663 A1 | 3/2009 |
| WO | 20090145690 A1 | 12/2009 |
| WO | 2018134372 A1 | 7/2018 |

OTHER PUBLICATIONS

Garcia-Gomez (Steriods and Related Compounds: basic and Clinical Aspects; Hindawi; vol. 2013).*
CDC (https://www.cdc.gov/fungal/diseases/index.html accessed May 21, 21).*
Doron ("Bacterial infections: Overview"; International Encyclopedia of Public Heatlh, 2008:273-282).*
National Institute of Health (https://www.niaid.nih.gov/research/antimicrobial-resistance-threats Feb. 11, 2020).*
International Search Report of the International Searching Authority for Application No. PCT/EP2018/051347, dated Apr. 17, 2018, 5 pages.
Written Opinion of the International Searching Authority for Application No. PCT/EP2018/051347, dated Apr. 17, 2018, 5 pages.
International Preliminary Report on Patentability for PCT/EP2018/051347, dated Apr. 30, 2019, 13 pages.
Illing, Biochemical and Biophysical Research Communications, 1993, 196(2), 745-51 (Year: 1993).
ITH/ISR Immune System Regulation: "An open phase II study in HIV-1 infected untreated male adult patients to evaluate safety and tolerability and the in vivo effects on T cell population and viral load of a GnRH analogue administrated by intranasal administration during 28 days when combined with a single intramuscular testosterone depot injection to restore a normal serum testosterone level", Apr. 30, 2014 (Apr. 30, 2014), pp. 1-13, XP055394073.
Millar et al., 1989 "Chimeric Analogues of Vertebrate Gonadotropin-releasing Hormones Comprising Substitutions of the Variant Amino Acids in Positions 5, 7, and 8. Characterization of requirements for receptor binding and gonadotropin release in mammalian and avian pituitary gonadotropes," J Biol Chem 264(35):21007-13.

(Continued)

*Primary Examiner* — James H Alstrum-Acevedo
*Assistant Examiner* — Tara L Martinez
(74) *Attorney, Agent, or Firm* — Fenwick & West LLP

(57) ABSTRACT

The present invention provides a method of treating intracellular infections, in particular intracellular bacterial, fungal, and protozoal infections.

20 Claims, 4 Drawing Sheets

Figure 1A:
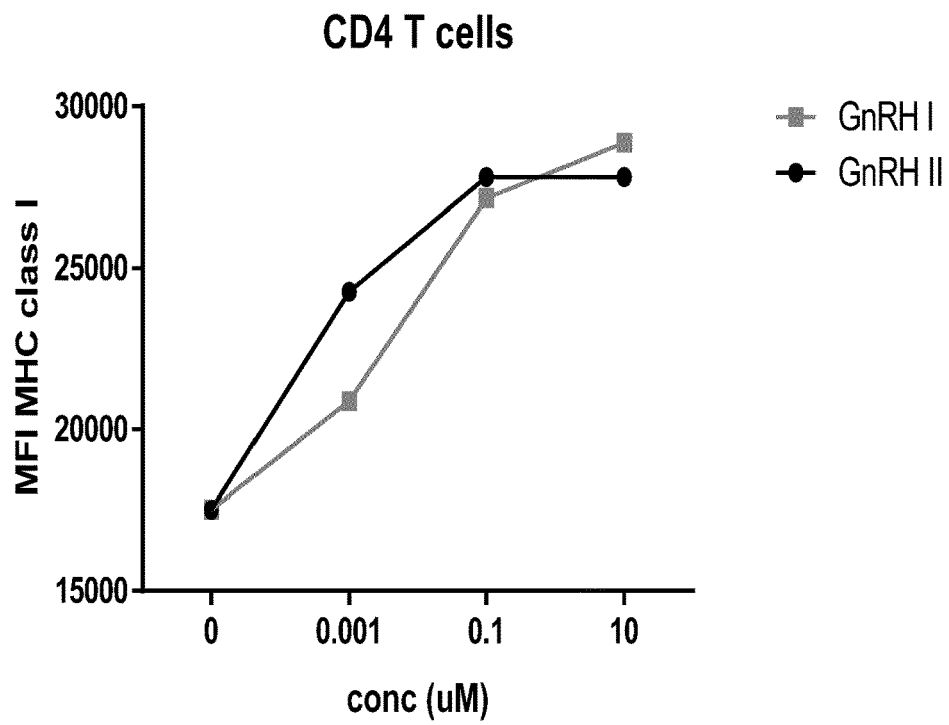

Specification includes a Sequence Listing.

(56) References Cited

OTHER PUBLICATIONS

Saussez et al., 2014 "Towards neuroimmunotherapy for cancer: the neurotransmitters glutamate, dopamine and GnRH-II augment substantially the ability of T cells of few head and neck cancer patients to perform spontaneous migration, chemotactic migration and migration towards the autologous tumor, and also elevate markedly the expression of CD3zeta and CD3epsilon TCR-associated chains," J Neural Transm (Vienna) 121(8):1007-27.

* cited by examiner

USE OF KNOWN COMPOUNDS—INTRACELLULAR INFECTIONS

FIELD OF THE INVENTION

The present invention provides a novel method of treating intracellular infections e.g. by bacteria, fungi, and protozoa using administration of GnRH or GnRH analogue and optionally one or more natural, semi-synthetic, or synthetic sex hormones.

BACKGROUND OF THE INVENTION

Intracellular bacterial, fungal, and protozoal infections are often not diagnosed in healthy individuals as they appear asymptomatic, or because the symptoms are mild enough that the infected individual is not inclined to seek medical assistance. As such, intracellular infections may persist latently or may progress to a disease state. Conditions interfering with normal T cell function usually leads to progression of the disease from a latent infection and intracellular infections such as *Mycobacterium tuberculosis* (Mtb) are a common cause of death in patients where HIV infection has progressed to AIDS. There is thus also a great need in the art for methods and means of treating intracellular infections.

Intracellular pathogens such as Mtb have the capacity to hide within intracellular compartments in monocytes and macrophages causing persistent infections. Although Mtb are recognized by CD4$^+$ T helper cells in the lung and an appropriate response is mounted, the system fails to create sterilizing immunity (MacMicking 2012). To escape immune recognition by the host, Mtb have developed a series of mechanism that inhibits recognition of Mtb peptides presented in the MHC class II pocket for CD4$^+$ T helper cells. Toll like receptor 2 has been demonstrated to be inhibited by Mtb, which in turn inhibits IFN-γ induced MHC class II expression (Noss 2001). In addition, data suggest that Mtb has the capacity to inhibit phagosome processing and maturation, possibly by an invariant chain associated mechanism (Ramachandra 2001). Therefore, the normal antigen processing, loading and presentation of MHC class II peptides derived from Mtb is impaired due to Mtb produced immune escape factors.

The endosomal lysosomal pathway is designed to take up pathogens, process them into 12-15 aa long peptides, peptides, that after the removal of the Invariant chain peptide CLIP by HLA-DM, are loaded into the MHC class II pocket. The antigen loading is followed by transport of the MHC class II-peptide complex to the cell surface for presentation for the specific T cell receptor of CD4$^+$ T helper cells (Roche 2015). Recently the Mtb expressed protein EsxH has been reported to directly inhibit the endosomal sorting complex required for transport (ESCRT) machinery (Portal-Celhay 2016). EsxH inhibits the ability of antigen presenting monocytes and macrophages to activate CD4$^+$ T helper cells. Since intact ESCRT machinery seems necessary for antigen processing, presentation and activation of T cells, EsxH is the link that explains Mtb induced immune escape by intervening with the MHC class II pathway.

The importance of MHC class II presentation has also been demonstrated in patients with primary immunodeficiencies (PID). PID patients with defects in the IFN-γ circuit, involving IFNGR, IL-12 have an increased of acquiring TBC and atypical mycobacterial infections. Since MHC class II expression is dependent and regulated by IFN-γ expression defects in the IFN-γ circuit will result in additionally decreased MHC class II expression and a poor activation of CD4$^+$ T helper cells.

Protozoa such as *Toxoplasma gondii* have developed a mechanism to avoid immune recognition by hiding intracellularly as an obligate intracellular parasite. The mechanism involves interference with MHC class II expression and thus diminish the amount of *Toxoplasma gondii* to be presented for specific CD4$^+$ T helper cells. The detailed mechanism is dependent on soluble proteins expressed by *Toxoplasma gondii* that inhibit IFN-gamma induced expression of MHC class II (Leroux 2015).

Furthermore, it has been demonstrated that different fungal infections are dependent on MHC class II expression. *Cryptococos neoformans* may cause life threatening brain infections in patients with immunodeficiencies including HIV. Work in a mouse model of *Cryptococos neoformans* has demonstrated that the activation of microglial cells and their upregulation of MHC class II, in an IFN-gamma dependent manner, is critical for survival (Zhou 2007).

Therefore, to overcome the immune escape mechanisms induced by Mtb and other intracellular bacteria, protozoa such as *Toxoplasma gondii*, or fungi exemplified by *Cryptococcus* an increased expression of MHC class II and MHC class I on the cell surface of monocytes, macrophages, microglia, or other infected cells is likely beneficial for immune recognition and elimination of the pathogen.

INTRODUCTION TO THE INVENTION

GnRH I (also known as gonadotropin releasing hormone or LHRH), is a decapeptide with the structure pyroGlu-His-Trp-Ser-Tyr-Gly-Leu-Arg-Pro-Gly-NH$_2$. It is produced as a 92 amino-acid propeptide which is modified post-translationally to form the final peptide with pyroglutamic acid at the amino terminus and a carboxamide at the carboxyl terminus. It has long been known that it is responsible for release of FSH and LH from the anterior pituitary gland, and is normally released from the hypothalamus in a pulsative manner. Suprasphysiological levels of GnRH I induce an immediate increase of FSH and LH secretion, soon followed by inhibition of FSH and LH secretion. This is due to the fact that high levels of GnRH I have an inhibitory effect on the type I GnRH receptors of the anterior pituary gland. Continuous administration of GnRH I at high unphysiological levels thus induces pharmacological castration (Fink 1998). A large number of GnRH I agonists and antagonists have been synthesized for use in therapeutic areas such as hormone sensitive cancer. Initially, salts of GnRH I were used therapeutically (such as gonadorelin hydrochloride and gonadorelin diacetate tetrahydrate). Further drug discovery and development led to the clinical use of a wide variety of agents, including buserelin, triptorelin, nafarelin, histrelin and leuprorelin, each of which has improvements over gonadorelin such as extended half-life and super-agonism of the type I GnRH receptor.

It has been reported that GnRH I not only exhibits hormonal effects but also may stimulate the immune system (Jacobson and Ansari 2004). McClean and McCluggage (McClean and McCluggage 2003) observed massive infiltration of small mature lymphocytes in uterine leiomyomas after preoperative treatment with a type I GnRH receptor agonist. Bardsley et al (Bardsley et al 2004) made the same observation, indicating a stimulatory effect on migration of GnRH I on the immune cells. Reports have been made on chronic plasma cell endometritis in hysterectomy specimens from HIV-infected women in a retrospective analysis (Kerr- Layton et al. 1998), and on elevated levels of FSH and LH (hypergonadotropic) in HIV-infected men (Arver et al 1999 and Brockmeyer eta/2000). By administering GnRH I to diabetes-prone BB rats exhibiting an AIDS-like lymphocyte profile the CD4 T-lymphocyte numbers was increased (Jacobson et al. 1999).

WO 2009/145690 A1 teaches us that GnRHs activate and upregulate MHC class I on T cells with the notion that HIV infected CD4 T cells down regulate MHC class I due to the HIV encoded protein Nef therefore avoiding recognition.

Figure 1B:
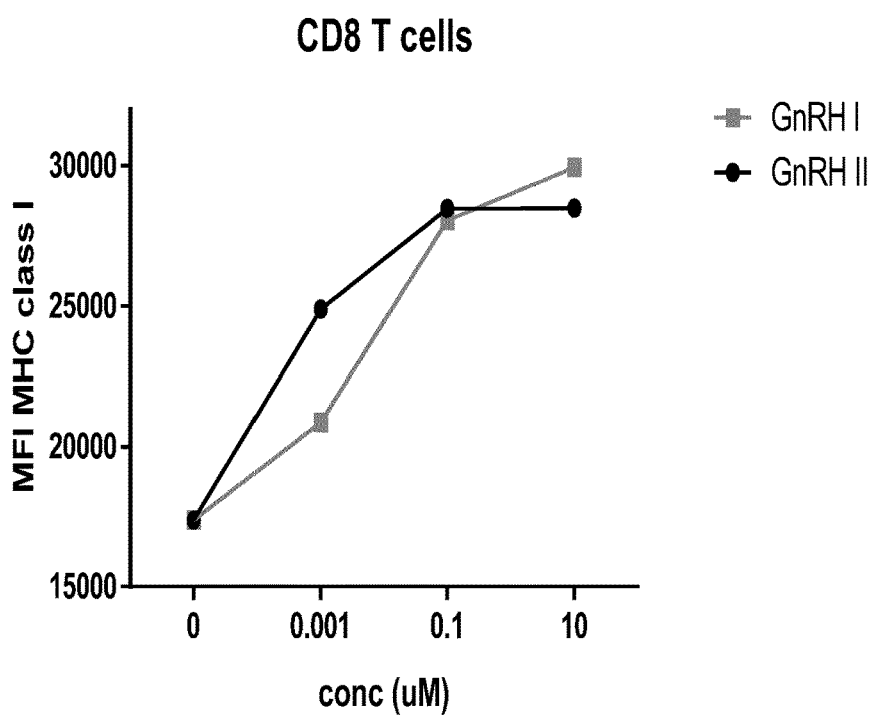
Figure 3:
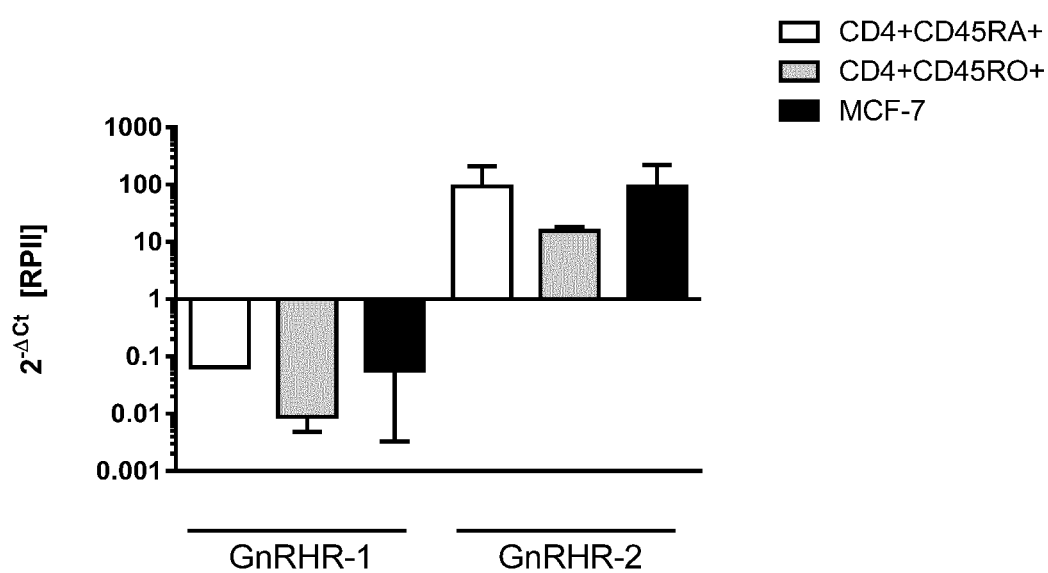

Unlike other mammals, only one conventional human GnRH receptor has been described, the type I GnRH receptor. The type II GnRH receptor homologue is present on chromosome 1q12 gene in humans but contains a frame shift and a stop codon and is believed not to be functionally expressed (Morgan et al 2003). Surprisingly, our findings suggest that the type II GnRH receptor is indeed expressed on T cells as they respond to GnRH stimulation by increased MHC class I expression (FIG. 1). These functional findings were substantiated by qPCR analysis where we could demonstrate expression of the type II GnRH receptor mRNA. In addition, the relative expression level of the type II GnRH receptor was higher compared to the expression levels of the type I GnRH receptor on naive and memory T cells (FIG. 3). Thus, we have identified that the expression of the type II GnRH receptor is the dominant receptor expressed on T cells, functionally responsive to GnRH stimulus.

DESCRIPTION OF THE INVENTION

We have also discovered that GnRH I analogs may activate T cells leading to MHC class I expression. In a recent clinical trial using the GnRH I analog Buserelin as treatment for HIV, HIV infected men were provided with sex hormone substitution to minimize the endocrine effects of GnRH I. These effects are mediated by GnRH I binding to pituitary type I GnRH receptors, causing decreased testosterone production and subsequently impotence. It is very likely that GnRH I in addition to its endocrine effects cross-signal and stimulate the immune system by binding to the type II GnRH receptor on T cells when high castrating levels of GnRH analogues are used. Interestingly, GnRH I binding to receptors expressed in breast cancer cells displays a low binding affinity (Kd, 1.6-3.0×10(−6) M), whereas central pituitary binding of GnRH I displays a 1000-fold higher affinity (Kd, 4.8×10(−9) M) (Eidne et al. 1987).

It is likely that the difference in binding affinity of GnRH I and GnRH II peptides reflects the expression of type I GnRH receptors specialised for GnRH I binding on pituitary cells, whereas peripheral cells may have dominated expression of type II GnRH receptor and therefore low affinity and an "off target" effect of GnRH I binding. Thus, our unexpected finding that the type II GnRH receptor is the dominating receptor on T cells is novel and may explain the receptor physiology of GnRH I and GnRH II. The GnRH or GnRH analogs may exhibit castrating effects when administered in effective doses, due to the activation of the type I GnRH receptor. The compounds may therefore be administered in combination with one or more natural, semi-synthetic or synthetic sex hormones to counter the endocrine effects of GnRH II-like peptides, e.g. testosterone or oestrogen depending on the hormonal status of the patient. In an adult male person the natural, semi-synthetic or synthetic sex hormone is testosterone or an agent having a corresponding hormonal effect. In an adult female person the natural, semi-synthetic or synthetic sex hormone is oestradiol or an agent having a corresponding hormonal effect, in particular in combination with a progestogen. The latter is added to avoid the development of endometrial cancer in the female and to avoid vaginal bleedings. Hysterectomized women, however, do not benefit from the addition of progestogen.

Viral peptides emerge in the cytosol and are targeted to the proteosome followed by processing and transport (TAP1 and TAP2) into the endoplasmatic reticulum where digested HIV peptides are added into the MHC class I peptide, followed by transport to the cell surface for presentation (Lubben et al., 2007).

Figure 2:
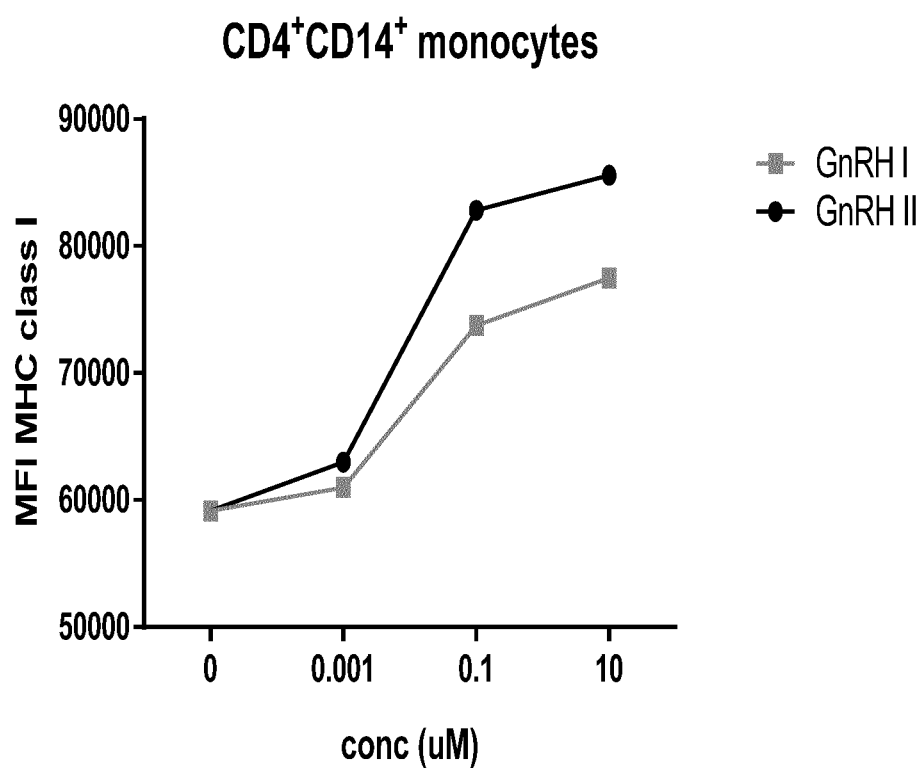

In contrast to the teaching of WO 2009/145690 A1 and in known art, intracellular bacteria are residents of the endosomal lysosmal pathway, a pathway normally not accessible for MHC class I in normal cells such as in T cells. However, in the present invention we demonstrate for the first time that GnRHs can upregulate MHC class I on antigen presenting cells (APCs) such as CD14+ monocytes (FIG. 2). APCs have the unique capability of cross presentation, i.e. they can present antigens from the endosomal lysosmal pathway into the MHC class I pocket, for activation of CD8+ T cells. This finding was surprising and suggests that intracellular bacteria such as *M Tuberculosis* which reside and hides in the endosomal lysosmal pathway of APCs. Thus, treating *M Tuberculosis* infected individuals with GnRHs will activate and stimulate APCs to initiate MHC class I upregulation by the cross-presentation pathway leading to recognition of *M Tuberculosis* peptides by CD8+ T cells and elimination of infected APCS.

In one aspect, the present invention provides a method for treating intracellular infections such as infections by intracellular bacteria, protozoa and fungi by use of one or more GnRH analogs. Intracellular bacteria to be treated include *Mycobacterium tuberculosis*, Mycobacteria causing atypical disease, *Mycobacterium avium* and *M. intracellulare* (also known as *Mycobacterium avium-intracellulare* complex, or MAC), *M. kansasii, M. marinum, M. fortuitum, M. gordinae, Mycoplasma pneumoniae, M. genitalium, M. hominis, Ureaplasma urealyticum, U. parvum, Chlamydophila pneumoniae*, and *Salmonella typhimurium*. Intracellular protozoa include *Toxoplasma gondii, Plasmodium falciparum, P. vivax, Trypanosoma cruzi, Cryptosporidium*, and *Leishmania*. Intracellular fungi include *Histoplasma capsulatum, Cryptococcus neoformans*, and *Encephalitozoon cuniculi*.

The compounds of the invention are contemplated to induce improved MHC II and/or MHC I antigen presentation, which make them useful in the treatment of intracellular bacterial, fungal, and protozoal infections. The present invention further provides a method for treating intracellular infection which comprises administration of an unphysiological amount of GnRH or a GnRH analog, and preferably also administering a sex hormone.

GnRH analogs are known in the art. A GnRH analog is an agent that mimics the action of GnRH on the receptors of the anterior pituitary gland when administered to an animal including man. Whereas administration of a GnRH analog in a single low physiological dose or in single low physiological doses spaced in time does stimulate the receptors of the anterior pituitary gland and thus acts as a receptor agonist, the continuous administration of a GnRH analog in a high unphysiological dose per time unit will, after initial stimulation of the receptors of the anterior pituitary gland, inhibit the secretion of FSH and LH, and thus acts as a receptor antagonist.

Known analogs for use according to the present invention include deslorelin, avorelin, leuprolide, triptorelin, buserelin, fertirelin, lutrelin, goserelin, historelin, and nafarelin.

Inhibition of FSH and LH secretion induces pharmacological castration. In this context, an unphysiological dose of GnRH or GnRH analog is a dose resulting in an unphysiological plasma level of GnRH or GnRH, respectively, in particular a castrating plasma level. In this context, an unphysiological plasma level of GnRH or GnRH analog is a level not comprised by range of levels of GnRH normally present or, in case of GnRH analogs, a level not comprised in regard of physiological effect by the normal physiological effect range of GnRH in a healthy person.

More particularly, in this context, an unphysiological plasma level of GnRH is a level increased, in particular increased for an extended period of time such as for more than a week or more than a month, in respect of the normal physiological plasma level of GnRH. Also, more particularly, an unphysiological plasma level of GnRH analog is an increased plasma level of GnRH analog not comprised in respect of physiological effect by the normal physiological effect range GnRH in a healthy person, in particular not for an extended period of time such as for more than a week or more than a month. Any useful form of administration of the GnRH or GnRH analog of the invention including their pharmaceutically acceptable salts is comprised by the invention, in particular intravenous, intramuscular, subcutaneous, sublingual, and nasal administration. Particular preferred are depot and slow or sustained release compositions.

To avoid undesired castrative or castrative-related side-effects, the GnRH or GnRH analogs may according to the present invention be administered in combination with one or more natural, semi-synthetic or synthetic sex hormones to counter the endocrine effects of GnRH II-like peptides, e.g. testosterone or oestrogen depending on the hormonal status of the patient. In an adult male person the natural, semi-synthetic or synthetic sex hormone is testosterone or an agent having a corresponding hormonal effect. In an adult female person the natural, semi-synthetic or synthetic sex hormone is oestradiol or an agent having a corresponding hormonal effect, in particular in combination with a progestogen. The latter is added to avoid the development of endometrial cancer in the female and to avoid vaginal bleedings. Hysterectomized women, however, do not benefit from the addition of progestogen.

The combined administration of one or more natural, semi-synthetic or synthetic sex hormones can be i) at the same time, i) the GnRH analog can be administered earlier than the sex hormone, or iii) the GnRH analog can be administered later than the sex hormone. Moreover, and dependent on the administration form used, the GnRH analog and/or the hormone may be administered more than one time such as eg in case of administration of the sex hormone via nasal spray, where administration typically is one or more times a day during one or more weeks.

The combined administration may extend, for instance, for over one or more periods interrupted by administration-free periods, or the administration can be continuous. A preferred administration period is from one to two weeks, in particular from 10 to 14 days. If a compound of the present invention has an endocrine effect by activating GnRH I it is preferred that the administration of said compound substantially overlaps the period of administration of one or more natural, semi-synthetic or synthetic sex hormones, such as by more than 50 percent, preferably by more than 85 percent, even more preferred by more than 90 or 95 percent. The combined administration allows to protect the person from serious endocrine side effects, such as decreased libido, hot flushes, increased perspiration, and increased heart rate. In an adult male person the natural, semi-synthetic or synthetic sex hormone administered to counter the endocrine effect of a compound of the invention is testosterone or an agent having a corresponding hormonal effect, in particular synthetic or semisynthetic agents that mimic the hormonal effects of testosterone. Preferred agents comprise methyltestosterone and stanozolol. In an adult female person the natural, semi-synthetic or synthetic sex hormone administered to counter the endocrine effect of a compound of the invention is an oestrogen such as oestradiol or a semi-synthetic ester of oestradiol or another synthetic or semi-synthetic oestrogen analog. Preferred oestrogen analogs comprise conjugated oestrogens, ethynylestradiol, and mestranol, as well as non-steroidal oestrogens such as dinestrol and diethylstilbestrol. In a female said oestrogen or oestrogen analog administration is in one aspect preferably combined with administration of a progestogen, in particular progesterone, a progesterone derivative or analog, such as hydroxyprogesterone caproate, medroxyprogesterone acetate, noethisterone acetate, megestrol acetate, medrogestone and norgestrel. The combined administration preferably overlaps by more than 50 percent, preferably by more than 85 percent, even more preferred by more than 90 or 95 percent. It is preferred that the progestogen to be administered in combination with the oestrogen, the semisynthetic ester of oestradiol or estriol or the synthetic or semisynthetic oestrogen analog continuously or over periods of from about 10 to 14 days in intervals from about one to three months.

Preferably a natural, semisynthetic, or synthetic sex hormone is administered in combination with a GnRH analog, and optionally with a pharmaceutically acceptable carrier. The compounds of the invention are contemplated to be of use in the treatment of intracellular bacterial, fungal, and protozoal infections, such as *Mycobacterium tuberculosis*, Mycobacteria causing atypical disease, *Mycobacterium avium* and *M. intracellulare* (also known as *Mycobacterium avium-intracellulare* complex, or MAC), *M. kansasii, M. marinum, M. fortuitum, M. gordinae, Mycoplasma pneumoniae, M. genitalium, M. hominis, Ureaplasma urealyticum, U. parvum, Chlamydophila pneumoniae*, and *Salmonella typhimurium*, and in the treatment of intracellular protozoal infections, such *Toxoplasma gondii, Plasmodium falciparum, P. vivax, Trypanosoma cruzi, Cryptosporidium*, and *Leishmania*, as well as in the treatment of intracellular fungal infections such as *Histoplasma capsulatum, Cryptococcus neoformans*, and *Encephalitozoon cuniculi*, when these infections occur alone or in association with viral agents or viral diseases, or in association with other causes of primary or secondary immunodeficiency. Causes of primary immunodeficiency include inherited genetic deficiencies and somatic mutations, whereas secondary immunodeficiency may be caused by viral infections such as those described above, or by inheritable or non-inheritable conditions such as Diabetes mellitus, or malnutrition, or by agents such as immunodepressants, drug abuse, or other environmental factors.

Moreover, the compounds of the invention disclosed herein may be used as a co-treatment of viral diseases, disorders, conditions, and symptoms, such as in treating patients infected with viral agents or with viral diseases such as HIV, Adenovirus, Alphavirus, Arbovirus, Borna Disease, Bunyavirus, Calicivirus, Condyloma Acuminata, Coronavirus, Coxsackievirus, Cytomegalovirus, Dengue fever virus, Contageous Ecthyma, Epstein-Barr virus, Erythema Infectiosum, Hantavirus, Viral Hemorrhagic Fever, Viral Hepatitis, Herpes Simplex Virus, Herpes Zoster virus, Infectious Mononucleosis, Influenza, Lassa Fever virus, Measles, Mumps, Molluscum Contagiosum, Paramyxovirus, Phlebotomus fever, Polyoma-virus, Rift Valley Fever, Rubella, Slow Disease Virus, Smallpox, Subacute Sclerosing Panencephalitis, Tumor Virus Infections, West Nile Virus, Yellow Fever Virus, Rabies Virus and Respiratory Syncitial Virus.

Moreover, the compounds are contemplated to be suitable for use in the co-treatment of cancer. In particular, Adrenal Cancer, Anal Cancer, Bile Duct Cancer, Bladder Cancer, Bone Cancer, Brain/CNS Tumors, Breast Cancer, Castleman Disease, Cervical Cancer, Colon/Rectum Cancer, Endometrial Cancer, Esophagus Cancer, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Acute Myeloid Leukemia, Chronic Lymphocytic Leukemia, Acute Lymphocytic Leukemia, Chronic Myeloid Leukemia, Chronic Myelomonocytic Leukemia, Liver Cancer, Non-Small Cell Lung Cancer, Small Cell Lung Cancer, Lung Carcinoid Tumor, Lymphoma, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Basal and Squamous Cell Skin Cancer, Melanoma, Merkel Cell Skin Cancer, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, Wilms Tumor.

Thus the advantageous properties of the compound of the invention may include one or more of the following:

Improved MHC class I stimulation
Improved MHC class II stimulation
Improved immunomodulation
Improved activation of antigen presenting cells
Improved T-cell response
Improved MHC II antigen presentation
Improved MHC I antigen presentation In the following list is given examples of known GnRH analogues:

| GnRH analogue | sequence |
|---|---|
| Avorelin | 5-oxo-Pro-His-Trp-Ser-Tyr-DTrp(2-Me)-Leu-Arg-NH(Et)-pro-linamide |
| Leuprolide | pGlu-His-Trp-Ser-Tyr-D-Leu-Leu-Arg-Pro-NHEt |
| Triptorelin | pGlu-His-Trp-Ser-Tyr-D-Trp-Leu-Arg-Pro-Gly-NH2 |
| Buserelin | Glu-His-Trp-Ser-Tyr-D-Ser(tBu)-Leu-Arg-Pro-NHEt |
| Fertirelin | Pyr-His-Trp-Ser-Tyr-Gly-Leu-Arg-Pro-NHEt |
| Lutrelin | H-Pyr-His-Trp-Ser-Tyr-D-Trp-N(Me)Leu-Arg-Pro-NHEt |
| Goserelin | H-Pyr-His-Trp-Ser-Tyr-D-Ser(tBu)-Leu-Arg-Pro-NHNHCONH2 |
| Histrelin | H-Pyr-His-Trp-Ser-Tyr-D-His(1-Bn)-Leu-Arg-Pro-NHEt |
| Narfarelin | H-DL-Pyr-DL-His-DL-Trp-DL-Ser-DL-Tyr-DL-2Nal-DL-Leu-DL-Arg-DL-Pro-Gly-NH2 |

Pharmaceutical Compositions Comprising a Compound of the Invention

The present invention also provides a pharmaceutical composition comprising the GnRH compound with one or more pharmaceutically acceptable diluents or carriers.

A composition may also contain both the GnRH compound and a sex hormone, but normally the administration regimes for the two types of drug substances are different and, accordingly, a composition in the form of a kit may be of greater relevance such as a kit comprising two components, where the first component is one or more GnRH-containing compositions and the second component is one or more sex hormone-containing compositions. The individual compositions contained in the kit may be of the same or different type. Thus, a composition of GnRH may be in the form of a parenteral or oral composition and a composition of a sex hormone may be in the form of a parenteral, nasal or oral composition.

Specific composition types for known GnRH or GnRH analogs as well as for sex hormones are known in the art.

The compounds or a formulation thereof may be administered by any conventional route for example but without limitation it may be administered parenterally, orally, topically or via a mucosa (including buccal, sublingual, transdermal, vaginal, rectal, nasal, ocular etc.), via a medical device (e.g. a stent), by inhalation. The treatment may consist of a single administration or a plurality of administrations over a period of time.

The treatment with GnRH may be by administration once daily, twice daily, three times daily, four times daily etc. dependent on the specific disease to be treated and the weight and age of the patient to be treated. The treatment may also be by continuous administration such as e.g. administration intravenous by infusion via a drop.

Whilst it is possible for the compounds of the invention to be administered as such, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

The formulations may conveniently be presented in a suitable dosage form including a unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compound of the invention will normally be administered by any conventional administration route normally by the oral or any parenteral route, in the form of a pharmaceutical formulation comprising the active ingredient, optionally in the form of a nontoxic organic, or inorganic, acid, or base, addition salt, in a pharmaceutically acceptable dosage form. Depending upon the disorder and patient to be treated, as well as the route of administration, the compositions may be administered at varying doses and/or frequencies.

The pharmaceutical compositions must be stable under the conditions of manufacture and storage; thus, if necessary should be preserved against the contaminating action of microorganisms such as bacteria and fungi. In case of liquid formulations such as solutions, dispersion, emulsions and suspensions, the carrier can be a solvent or dispersion medium containing, for example, water, ethanol, polyol (e.g. glycerol, propylene glycol and liquid polyethylene glycol), vegetable oils, and suitable mixtures thereof.

For example, the compound of the invention may be administered orally, buccally or sublingually in the form of tablets, capsules, films, ovules, elixirs, solutions, emulsions or suspensions, which may contain flavouring or colouring agents.

Formulations in accordance with the present invention suitable for oral administration may be presented as discrete units such as capsules, cachets or tablets, each containing a predetermined amount of the active ingredient; as multiple units e.g. in the form of a tablet or capsule: as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Solutions or suspensions of the compound of the invention suitable for oral administration may also contain one or more solvents including water, alcohol, polyol etc. as well as one or more excipients such as pH-adjusting agent, stabilizing agents, surfactants, solubilizers, dispersing agents, preservatives, flavors etc. Specific examples include e.g. N,N-dimethylacetamide, dispersants e.g. polysorbate 80, surfactants, and solubilisers, e.g. polyethylene glycol, Phosal 50 PG (which consists of phosphatidylcholine, soya-fatty acids, ethanol, mono/diglycerides, propylene glycol and ascorbyl palmitate).

The formulations according to present invention may also be in the form of emulsions, wherein a compound according to Formula (I) may be present in an emulsion such as an oil-in-water emulsion or a water-in-oil emulsion. The oil may be a natural or synthetic oil or any oil-like substance such as e.g. soy bean oil or safflower oil or combinations thereof.

Tablets may contain excipients such as microcrystalline cellulose, lactose (e.g. lactose monohydrate or lactose anhydrous), sodium citrate, calcium carbonate, dibasic calcium phosphate and glycine, butylated hydroxytoluene (E321), crospovidone, hypromellose, disintegrants such as starch (preferably corn, potato or tapioca starch), sodium starch glycollate, croscarmellose sodium, and certain complex silicates, and granulation binders such as polyvinylpyrrolidone, hydroxypropylmethylcellulose (HPMC), hydroxypropylcellulose (HPC), macrogol 8000, sucrose, gelatin and acacia. Additionally, lubricating agents such as magnesium stearate, stearic acid, glyceryl behenate and talc may be included.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either colloidal, suspended or dissolved in the vehicle. In preparing solutions the active ingredient can be dissolved in water for injection and filter sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

It should be understood that in addition to the ingredients particularly mentioned above the formulations of this invention may include other agents conventional in the art having regard to the type of formulation in question, for example those suitable for oral administration may include flavouring agents. A person skilled in the art will know how to choose a suitable formulation and how to prepare it (see eg Remington's Pharmaceutical Sciences 18 Ed. or later). A person skilled in the art will also know how to choose a suitable administration route and dosage.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

A pharmaceutical composition may also be a two-part composition, where one part contains the GnRH analog and the other part contains the sex hormone. The two parts may be combined eg as a two-layer tablet or they may be present eg as pellets in a capsule. Known compositions containing a GnRH analog and known compositions containing a sex hormone may also be used in a method of the invention.

All % values mentioned herein are % w/w unless the context requires otherwise.

Sequence List

The sequence list is prepared according to the WIPO standard ST.25. In the sequence list, the unnatural amino acids of compounds 1-10 are represented as the corresponding natural amino acid in the following way:

| Unnatural amino acid | Corresponding natural amino acid |
|---|---|
| pGlu, pyroglutamate, H-Pyr, Pyr | L-Glutamate, Glu |
| 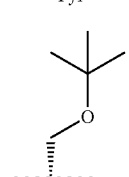 D-Ser(OtBu) | L-Serine, Ser |
| 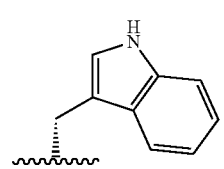 D-Trp | L-Tryptophan, Trp |
| 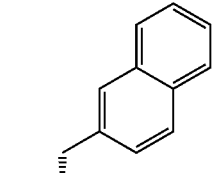 D-Nal | L-Phenylalanine, Phe |

| Unnatural amino acid | Corresponding natural amino acid |
|---|---|
| 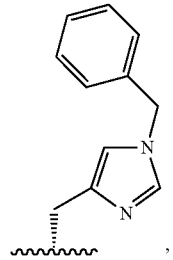 D-Bhi | L-Histidine, His |
| 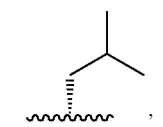 D-Leu | L-Leucine, Leu |
| Pro-Et | L-Proline, Pro |
| Pro-NHNHCONH$_2$ | L-Proline, Pro |
| Gly-NH$_2$ | Gly |
| 5-oxo-Pro | Pro |
| D-Trp-(2Me) | Trp |

In the sequence list, entries 1-10 correspond to known compounds mentioned in the table herein. However, the sequences SEQ ID Nos: 1-16 as they are stated in the sequence list, i.e. without above-described unnatural amino acids, are not claimed, but are included only to comply with the requirements of R. 30(1) of the EPC.

Repetition of Free Text from Sequence Listing

For compliance with paragraph 36 of WIPO Standard ST.25, the free text included under numeric identifier <223> of the sequence listing is hereby repeated in the main part of the description:

| SEQ ID NO | Free text included in <223> |
|---|---|
| 1-10 | Man-made analogue of GnRH |
| 11 | GnRH I |
| 12 | GnRH II |
| 13 | Type I GnRH Receptor forward primer |
| 14 | Type I GnRH Receptor reverse primer |
| 15 | Type II GnRH Receptor forward primer |
| 16 | Type II GnRH Receptor reverse primer |

Definitions

The articles "a" and "an" are used herein to refer to one or to more than one (i.e. at least one) of the grammatical objects of the article. By way of example "an analogue" means one analogue or more than one analogue.

The pharmaceutically acceptable salts of the compound of the invention include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

LEGENDS TO FIGURES

FIG. 1 Expression of MHC class I after stimulation of T cells with increasing concentrations of GnRH I analogue (red) and GnRH II (black). PBMCs from a healthy donor was stimulated with GnRH I analogue or with GnRH II and IL-2 for 72 hours. Data points represent mean fluorescent intensity of MCH class I expression on $CD4^+$ T cells (A) or $CD8^+$ T cells (B) measured with flow cytometry.

FIG. 2: Expression of MHC class I after stimulation of $CD4^+CD14^+$ monocytes with increasing concentrations of GnRH I analogue (red) and GnRH II (black). $CD14^+$ monocytes PBMCs from a healthy donor was stimulated with GnRH I analogue or with GnRH II and IL-2 for 72 hours. Data points represent mean fluorescent intensity of MCH class I expression on $CD4^+CD14^+$ monocytes measured with flow cytometry.

FIG. 3: GnRH receptor expression in human T cells analysed with quantitative real-time PCR. The bars represent ratios of type I or type II GnRH Receptor mRNA normalized to RNA polymerase II expression in sorted naive T cells (white bars) or memory T cells (gray bars). MCF-7 breast cancer cell line (black bar) was used as a positive control.

Figure 4:
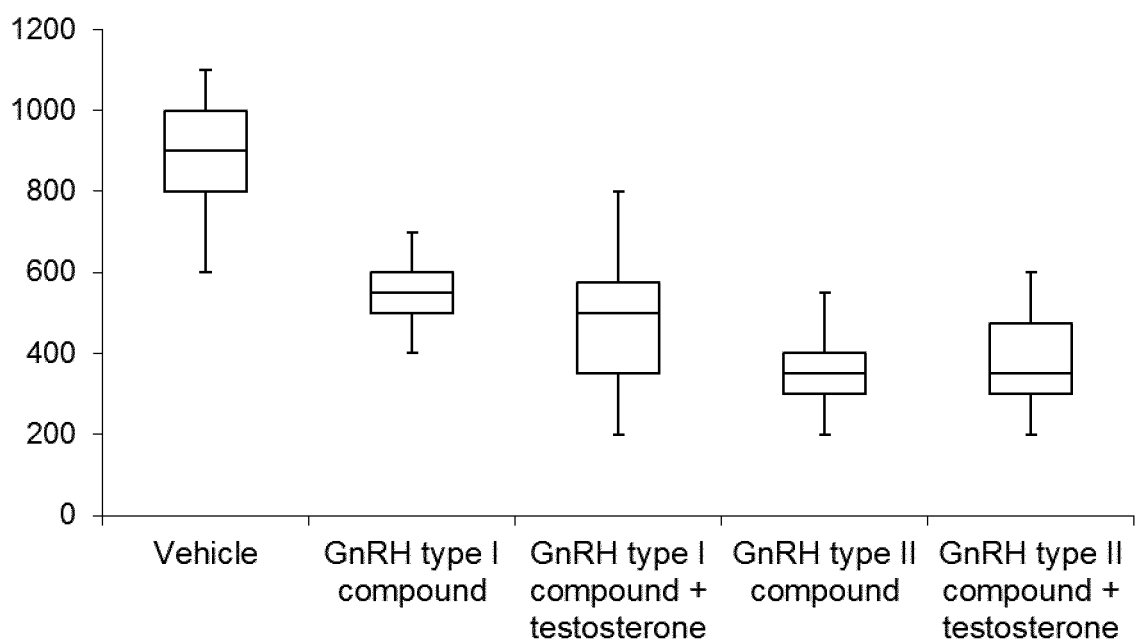

FIG. 4: Expected data: Number of mycobacteria in the lungs of infected mice are suppressed by GnRH related compounds in the presence or absence of testosterone. Colony Forming Units (CFU) are asessed by growing lysates of lung tissue from infected mice on bacterial plates and counting colonies.

EXPERIMENTAL

General Biology Methods

The preferential effect of the compounds of the invention on GnRH receptors may be tested using one or more of the methods described below:

I. Expression of GnRH Receptors on T Cells

Human naive and memory T cells were labeled with fluorescent surface marker antibodies CD45RA, CD45RO and CD4 and sorted with flow cytometry. Total RNA was extracted with Rneasy kit (Qiagen) and reverse transcribed with iScript select cDNA synthesis kit (Biorad). The template cDNA was amplified with SYBR Green (Applied Biosystem) and run on CFX96 PCR (Biorad). Ratios of Type I GnRH Receptor and Type II GnRH Receptor mRNA were normalized to RNA polymerase II expression in sorted naive T cells or memory T cells. The MCF-7 breast cancer cell line was used as a positive control.

Primer Sequences:

```
Type I GnRH Receptor
fwd      5'-tgc ctc ttc atc atc cct ct-3' rev      5'-gca aat gca acc gtc att tt-3'

Type II GnRH Receptor
fwd      5'-act gtt caa tgg ctg gct gt-3' rev      5'-gcc ccc aga agt ttc ctt ac-3'
```

I. GnRH I Vs GnRH II Assay

Compounds were tested on cells made to express Type I or Type II GnRH Receptors by transfection. The cells were exposed to labelled GnRH compound, washed and then assessed by measuring the label on the cells. The label was either measured directly (radioactive isotope label or fluorescent label) or indirectly (biotin labelled peptide).

Signalling induced by the GnRH compounds was measured in the cell lines expressing Type I GnRH and Type II GnRH Receptors respectively. GnRH compounds were investigated for their respective affinity to type I GnRH receptors and type II GnRH receptors using competition assays. Calcium flux was measured using cells labelled with Fluo-4-Direct either using a flow cytometer or by live cell imaging microscopy, in order to evaluate their potency establishing ED50 values. Signalling was also studied by western blotting using antibodies to p-ERK or p-JNK.

To assess the effects of cellular activation on the production of LH and FSH and compare it with stimulation of immune related functions, the effects of the compounds were studied on pituitary cells and immune cells expressing either Type II GnRH or Type I GnRH Receptors.

I. Expression of Cell Specific Surface Markers and MHC Class II and MHC Class I

Human peripheral blood mononuclear cells (PBMCs) were purified from healthy donors with Ficoll-Hypaque density centrifugation. Cells were cultured in RPMI-1640 medium (Invitrogen) supplemented with 10% fetal bovine serum, 100 µg/mL ampicilin and 100 µg/mL streptomycin for 24-72 hours in 37° C., 5% $CO_2$. Cells were stimulated with a compound according to the invention and analysed for expression of cell specific surface markers and MHC class II (monoclonal antibodies from BD Pharmingen) with flow cytomtery.

To test a set of compounds according to the invention for their immunomodulatory properties in an in vitro assay and evaluate their ability to induce MHC class II expression on monocytes. First when a known GnRH analogue was used in a co-culture to stimulate monocytes. A small increase in MHC class expression from background of in MFI may be seen. In contrast, when a compound according to the invention is used we may detect a larger expression of cell surface expression of MHC class II and class I, thus allowing increased turnover and presentation of MHC class II and class I peptides from the endosomal and lysosomal pathway. The findings will enhance the presentation of peptides derived from intracellular pathogens and promote $CD4^+$ T helper as well as CD8+ T cells activation, expansion and induce sterilizing immunity.

Theoretical Example of GnRHII Compound on Intracellular Bacteria

Material and Methods

Male mice are infected with *Mycobacterium tuberculosis* by inhalation of an aerosol containing the bacteria. The infecting dose is between 100 and 1000 bacteria per mouse. The GnRHII or GnRHI related compound (alone or together with testosterone) or vehicle is administered by an appropriate route in an appropriate dose for 1-2 weeks after infection with the bacteria. The mice are sacrificed and lungs removed and homogenized and plated on bacteria dishes containing medium that supports the growth of *Mycobacterium tuberculosis*, such as e.g. Löwenstein-Jensen medium, Dubos' medium, Middlebrook 7H10, 7H11, or 7H9, Sula's Medium, or the like. Persons skilled in the art will know how to select a suitable medium. After 3-4 weeks incubation, in a heated cabinet at 37 degrees C., the amount of bacteria in the lungs of the mice are quantified by counting bacterial colonies on the plate. The skilled person will know of other methods of quantifiying bacteria.

Expected Results

Expected results of this experiments is that the amount of *Mycobacterium tuberculosis* bacteria in the lungs of mice are reduced in mice treated with GnRH compounds compaired with control vehicle treated mice. We also expect GnRHII related compounds to be superior to GnRHI related compounds in this respect. We do not expect co-administration of testosterone will have any effect on the degree of effect of the GnRH compounds.

Measurement of Castractive Effects and Compensation Thereof

Castration induced by the compounds of the invention, as well as any compensation thereof can be determined by measurement of the circulating levels of the relevant sex hormones. How to carry out such measurements is known to the person skilled in the art.

REFERENCES

Interferon-inducible effector mechanisms in cellautonomous immunity. MacMicking, J. D. Nat. Rev. Immunol. 12, 367-382 (2012).

Toll-like receptor 2-dependent inhibition of macrophage class II MHC expression and antigen processing by 19-kDa lipoprotein of *Mycobacterium tuberculosis*. Noss, E. H. et al. J. Immunol. 167, 910-918 (2001).

HIV-1 Nef-induced Down-Regulation of MHC Class I Requires AP-1 and Clathrin but Not PACS-1 and Is Impeded by AP-2. Lubben, N. B. et al. Mol Biol. Cell. 18 (3351-3365).

Processing of *Mycobacterium tuberculosis* antigen 85B involves intraphagosomal formation of peptide-major histocompatibility complex II complexes and is inhibited by live bacilli that decrease phagosome maturation. Ramachandra, L., Noss, E., Boom, W. H. & Harding, C. V. J. Exp. Med. 194, 1421-1432 (2001).

The ins and outs of MHC class II-mediated antigen processing and presentation. Roche P A & Furuta K. *Nature Reviews Immunology* 15, 203-216 (2015)

Secreted *Toxoplasma gondii* molecules interfere with expression of MHC-II in interferon gamma-activated macrophages. Leroux L-P, Dasanayake D, Rommerein L M, Fox B A, Bzik D J, Jardim A, Dzierszinski F S. *International Journal for Parasitology* 2015 45: 319-332

Protection form Direct Cerebral *Cryptococcus* Infection by Interferon gamma-dependent Activation of Microglial Cells. Zhou Q, Gault R A, Kozel T R, Murphy W J. *The Journal of Immunology* 2007: 178: 5753-5761

*Mycobacterium tuberculosis* EsxH inhibits ESCRT-dependent CD4+ T-cell activation Portal-Celhay C, Tufariello J A M, Srivastava S, Zahra A, Klevorn T, Grace P S, Mehra A, Park H S, Ernst J D, Jacobs Jr W R & Philips J A. *Nature Microbiology* 2, Article number: 16232 (2016) doi:10.1038/nmicrobiol.2016.232

Gonadotropin secretion and its control. Fink G, The physiology of reproduction 1998.

Immunomodulatory actions of gonadal steroids may be mediated by gonadotropin-releasing hormone. Jacobson J D and Ansari M A, Endocrinology 2004; 145(1):330-6.

Unusual morphologic features of uterine leiomyomas treated with gonadotropin-releasing hormoneagonists: massive lymphoid infiltration and vasculitis. McClean G and McCluggage W G, Int J Surg Pathol. 2003; 11(4): 339-44.

Massive lymphocytic infiltration of uterine leyomyomas associated with GnRH agonist treatment. Bardsley V et al., Histopathology 1998; 33(1):80-2.

Chronic plasma cell endometritis in hysterectomy specimens of HIV-infected women: a retrospective analysis. Kerr-Layton J A et al., Infect Dis Obstet Gynecol. 1998; 6(4):186-90.

Serum dihydrotestosterone and testosterone concentrations in human immunodeficiency virus-infected men with and without weight loss. Arver S et al., J Androl 1999; 20(5):611-8.

Prevalence of endocrine dysfunction in HIV-infected men. Brockmeyer G et al., Horm Res 2000; 54(5-6):294-5.

Gonadotropin-releasing hormone increases CD4-T-lymphocyte numbers in an animal model of immunodeficiency. Jacobson J D et al., J Allergy Clin Immunol. 1999; 104:653-8.

A transcriptionally active human type II gonadotropin-releasing hormone receptor gene homolog overlaps two genes in the antisense orientation on chromosome 1q.12. Morgan et al., Endocrinology. 2003 February; 144(2): 423-36 Gonadotropin-releasing hormone (GnRH)-binding sites in human breast cancer cell lines and inhibitory effects of GnRH antagonists. Eidne et al., J Clin Endocrinol Metab. 1987 March; 64(3):425-32

All references referred to in this application, including patent and patent applications, are incorporated herein by reference to the fullest extent possible.

The invention claimed is:

1. A method of treating or preventing an intracellular infection in a subject in need thereof, comprising administering to the subject an effective amount of a GnRH or a GnRH analog in combination with a sex hormone; wherein the intracellular infection is selected from *Mycobacterium tuberculosis*, Mycobacteria causing atypical disease, *Mycobacterium avium* and *M. intracellulare* (also known as *Mycobacterium avium-intracellulare* complex, or MAC), *M. kansasii*, *M. marinum*, *M. fortuitum*, *M. gordinae*, *Mycoplasma pneumoniae*, *M. genitalium*, *M. hominis*, *Ureaplasma urealyticum*, *U. parvum*, *Chlamydophila pneumoniae*, *Salmonella typhimurium*, *Toxoplasma gondii*, *Plasmodium falciparum*, *P. vivax*, *Trypanosoma cruzi*, *Cryptosporidium*, *Leishmania*, *Histoplasma capsulatum*, *Cryptococcus neoformans*, and *Encephalitozoon cuniculi*.

2. The method according to claim 1, comprising administering a GnRH analog, wherein the GnRH analog is selected from deslorelin, avorelin, leuprolide, triptorelin, buserelin, fertirelin, lutrelin, goserelin, histrelin, and nafarelin or a pharmaceutically acceptable salt thereof.

3. The method according to claim 1, wherein the subject is a female subject, and wherein the sex hormone is selected from oestradiol, a semi-synthetic ester of oestradiol, and a synthetic or semi-synthetic oestrogen analog.

4. The method according to claim 3, comprising administering a GnRH analog, wherein the GnRH analog is selected from deslorelin, avorelin, leuprolide, triptorelin, buserelin, fertirelin, lutrelin, goserelin, histrelin, and nafarelin or a pharmaceutically acceptable salt thereof.

5. The method according to claim 1, wherein the subject is a male subject, and wherein the sex hormone is selected from testosterone and a testosterone analog.

6. The method according to claim 5, comprising administering a GnRH analog, wherein the GnRH analog is selected from deslorelin, avorelin, leuprolide, triptorelin, buserelin, fertirelin, lutrelin, goserelin, histrelin, and nafarelin or a pharmaceutically acceptable salt thereof.

7. The method according to claim 1, wherein administration of said sex hormone compensates for a castractive effect of said GnRH or GnRH analog.

8. The method according to claim 1, wherein the subject is treated with the GnRH or GnRH analog for a treatment period of one month or longer.

9. The method according to claim 8, wherein the subject is treated with the GnRH or GnRH analog for a treatment period of half a year or longer.

10. The method according to claim 9, wherein the subject is treated with the GnRH or GnRH analog for a treatment period of a year or longer.

11. The method according to claim 8, comprising administering a GnRH analog, wherein the GnRH analog is selected from deslorelin, avorelin, leuprolide, triptorelin, buserelin, fertirelin, lutrelin, goserelin, histrelin, and nafarelin or a pharmaceutically acceptable salt thereof.

12. The method according to claim 1, comprising oral, intramuscular, subcutaneous, sublingual, or nasal administration of the GnRH, GnRH analog, or sex hormone.

13. The method according to claim 1, wherein the subject is an adult female, and wherein the sex hormone is an oestrogen.

14. The method of claim 13, further comprising administering a progestogen to the subject.

15. The method according to claim 14, comprising administering a GnRH analog, wherein the GnRH analog is selected from deslorelin, avorelin, leuprolide, triptorelin, buserelin, fertirelin, lutrelin, goserelin, histrelin, and nafarelin or a pharmaceutically acceptable salt thereof.

16. The method according to claim 13, comprising administering a GnRH analog, wherein the GnRH analog is selected from deslorelin, avorelin, leuprolide, triptorelin, buserelin, fertirelin, lutrelin, goserelin, histrelin, and nafarelin or a pharmaceutically acceptable salt thereof.

17. The method according to claim 1, wherein the subject is a female subject.

18. The method according to claim 17, comprising administering a GnRH analog, wherein the GnRH analog is selected from deslorelin, avorelin, leuprolide, triptorelin, buserelin, fertirelin, lutrelin, goserelin, histrelin, and nafarelin or a pharmaceutically acceptable salt thereof.

19. The method according to claim 1, wherein the subject is a male subject.

20. The method according to claim 19, comprising administering a GnRH analog, wherein the GnRH analog is selected from deslorelin, avorelin, leuprolide, triptorelin, buserelin, fertirelin, lutrelin, goserelin, histrelin, and nafarelin or a pharmaceutically acceptable salt thereof.

* * * * *

SEQUENCE LISTING

```
<160> NUMBER OF SEQ ID NOS: 16

<210> SEQ ID NO 1
<211> LENGTH: 9
<212> TYPE: PRT
<213> ORGANISM: Artificial Sequence
<220> FEATURE:
<223> OTHER INFORMATION: P1

<400> SEQUENCE: 1
```

Glu His Trp Ser Tyr Trp Leu Arg Pro
1               5

<210> SEQ ID NO 2
<211> LENGTH: 9
<212> TYPE: PRT
<213> ORGANISM: Artificial Sequence
<220> FEATURE:
<223> OTHER INFORMATION: P2

<400> SEQUENCE: 2

Pro His Trp Ser Tyr Trp Leu Arg Pro
1               5

<210> SEQ ID NO 3
<211> LENGTH: 9
<212> TYPE: PRT
<213> ORGANISM: Artificial Sequence
<220> FEATURE:
<223> OTHER INFORMATION: p3

<400> SEQUENCE: 3

Glu His Trp Ser Tyr Leu Leu Arg Pro
1               5

<210> SEQ ID NO 4
<211> LENGTH: 10
<212> TYPE: PRT
<213> ORGANISM: Artificial Sequence
<220> FEATURE:
<223> OTHER INFORMATION: p4

<400> SEQUENCE: 4

Glu His Trp Ser Tyr Trp Leu Arg Pro Gly
1               5                   10

<210> SEQ ID NO 5
<211> LENGTH: 9
<212> TYPE: PRT
<213> ORGANISM: Artificial Sequence
<220> FEATURE:
<223> OTHER INFORMATION: p5

<400> SEQUENCE: 5

Glu His Trp Ser Tyr Ser Leu Arg Pro
1               5

<210> SEQ ID NO 6
<211> LENGTH: 9
<212> TYPE: PRT
<213> ORGANISM: Artificial Sequence
<220> FEATURE:
<223> OTHER INFORMATION: p6

<400> SEQUENCE: 6

Glu His Trp Ser Tyr Gly Leu Arg Pro
1               5

<210> SEQ ID NO 7
<211> LENGTH: 9
<212> TYPE: PRT
<213> ORGANISM: Artificial Sequence
<220> FEATURE:
<223> OTHER INFORMATION: p7

<400> SEQUENCE: 7

Glu His Trp Ser Tyr Trp Leu Arg Pro

```
1               5
```

<210> SEQ ID NO 8
<211> LENGTH: 10
<212> TYPE: PRT
<213> ORGANISM: Artificial Sequence
<220> FEATURE:
<223> OTHER INFORMATION: p8

<400> SEQUENCE: 8

```
Glu His Trp Ser Tyr Ser Leu Arg Pro Gly
1               5                   10
```

<210> SEQ ID NO 9
<211> LENGTH: 9
<212> TYPE: PRT
<213> ORGANISM: Artificial Sequence
<220> FEATURE:
<223> OTHER INFORMATION: p9

<400> SEQUENCE: 9

```
Glu His Trp Ser Tyr His Leu Arg Pro
1               5
```

<210> SEQ ID NO 10
<211> LENGTH: 10
<212> TYPE: PRT
<213> ORGANISM: Artificial Sequence
<220> FEATURE:
<223> OTHER INFORMATION: p10

<400> SEQUENCE: 10

```
Glu His Trp Ser Tyr Phe Leu Arg Pro Gly
1               5                   10
```

<210> SEQ ID NO 11
<211> LENGTH: 10
<212> TYPE: PRT
<213> ORGANISM: Homo sapiens
<220> FEATURE:
<223> OTHER INFORMATION: GnRH I

<400> SEQUENCE: 11

```
Glu His Trp Ser Tyr Gly Leu Arg Pro Gly
1               5                   10
```

<210> SEQ ID NO 12
<211> LENGTH: 10
<212> TYPE: PRT
<213> ORGANISM: Homo sapiens
<220> FEATURE:
<223> OTHER INFORMATION: GnRH II

<400> SEQUENCE: 12

```
Glu His Trp Ser His Gly Trp Tyr Pro Gly
1               5                   10
```

<210> SEQ ID NO 13
<211> LENGTH: 20
<212> TYPE: DNA
<213> ORGANISM: Homo sapiens
<220> FEATURE:
<223> OTHER INFORMATION: Type I GnRH Receptor forward primer

<400> SEQUENCE: 13

```
tgcctcttca tcatccctct                                                   20
```

```
<210> SEQ ID NO 14
<211> LENGTH: 20
<212> TYPE: DNA
<213> ORGANISM: Homo sapiens
<220> FEATURE:
<223> OTHER INFORMATION: Type I GnRH Receptor reverse primer

<400> SEQUENCE: 14
gcaaatgcaa ccgtcatttt                                              20

<210> SEQ ID NO 15
<211> LENGTH: 20
<212> TYPE: DNA
<213> ORGANISM: Homo sapiens
<220> FEATURE:
<223> OTHER INFORMATION: Type II GnRH Receptor forward primer

<400> SEQUENCE: 15
actgttcaat ggctggctgt                                              20

<210> SEQ ID NO 16
<211> LENGTH: 20
<212> TYPE: DNA
<213> ORGANISM: Homo sapiens
<220> FEATURE:
<223> OTHER INFORMATION: Type II GnRH Receptor reverse primer

<400> SEQUENCE: 16
gcccccagaa gtttccttac                                              20
```